United States Patent
Jolly et al.

(10) Patent No.: US 6,682,934 B2
(45) Date of Patent: Jan. 27, 2004

(54) AUTOMATED AIRBORNE METAL ANALYZER

(75) Inventors: Clifford Jolly, Parker, CO (US); Leslie A. Karr, Oak View, CA (US); Bryan Lee Harre, Oxnard, CA (US); Barbara Marie Sugiyama, Oxnard, CA (US); John Joseph Kornuc, Malibu, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 320 days.

(21) Appl. No.: 09/972,297

(22) Filed: Oct. 1, 2001

(65) Prior Publication Data

US 2003/0064529 A1 Apr. 3, 2003

(51) Int. Cl.$^7$ .............................................. G01N 33/20
(52) U.S. Cl. .............................. 436/73; 436/79; 436/80; 436/81; 436/82; 436/83; 436/84; 436/177; 436/181; 422/83; 422/88; 422/90; 422/91; 422/92
(58) Field of Search ...................... 422/83, 88, 90–92; 436/73, 77, 79–84, 167, 171, 172, 177, 181

(56) References Cited

U.S. PATENT DOCUMENTS

| | | | |
|---|---|---|---|
| 4,249,904 A | * 2/1981 | Rounbehler et al. | 436/178 |
| 4,759,210 A | * 7/1988 | Wohltjen | 73/31.07 |
| 4,961,916 A | * 10/1990 | Lesage et al. | 422/88 |
| 5,173,264 A | * 12/1992 | Zaromb et al. | 422/88 |
| 5,479,359 A | * 12/1995 | Rogero et al. | 702/24 |
| 5,514,593 A | * 5/1996 | Townsend et al. | 436/77 |
| 5,597,535 A | * 1/1997 | Schaedlich et al. | 422/88 |
| 5,873,990 A | * 2/1999 | Wojciechowski et al. | 204/406 |
| 6,087,183 A | * 7/2000 | Zaromb | 436/178 |
| 6,200,816 B1 | * 3/2001 | Farber et al. | 436/73 |

* cited by examiner

Primary Examiner—Arlen Soderquist
(74) Attorney, Agent, or Firm—David S. Kalmbaugh

(57) ABSTRACT

A portable instrument for automatic collection and analysis of airborne lead concentrations in ambient air environments. Its improvements to the art of airborne lead detection and analysis permit the apparatus to analyze samples previously collected by personal monitors, for example, worn on the clothing of personnel working in contaminated sites. The apparatus also brings to the art of lead analysis a method of contaminant collection that ensures a greater capture efficiency of airborne contaminants, thereby increasing the accuracy of the instrument and its measurement capabilities while providing near real-time analysis and measurement in a portable self-contained battery-powered device. The apparatus also offers a remarkable improvement in the reduction of wastes incurred in the collection and analysis of airborne lead contaminants which is a novel method of concentrating the samples and recycling the analysis media used to concentrate and solubilize lead contaminants.

8 Claims, 1 Drawing Sheet

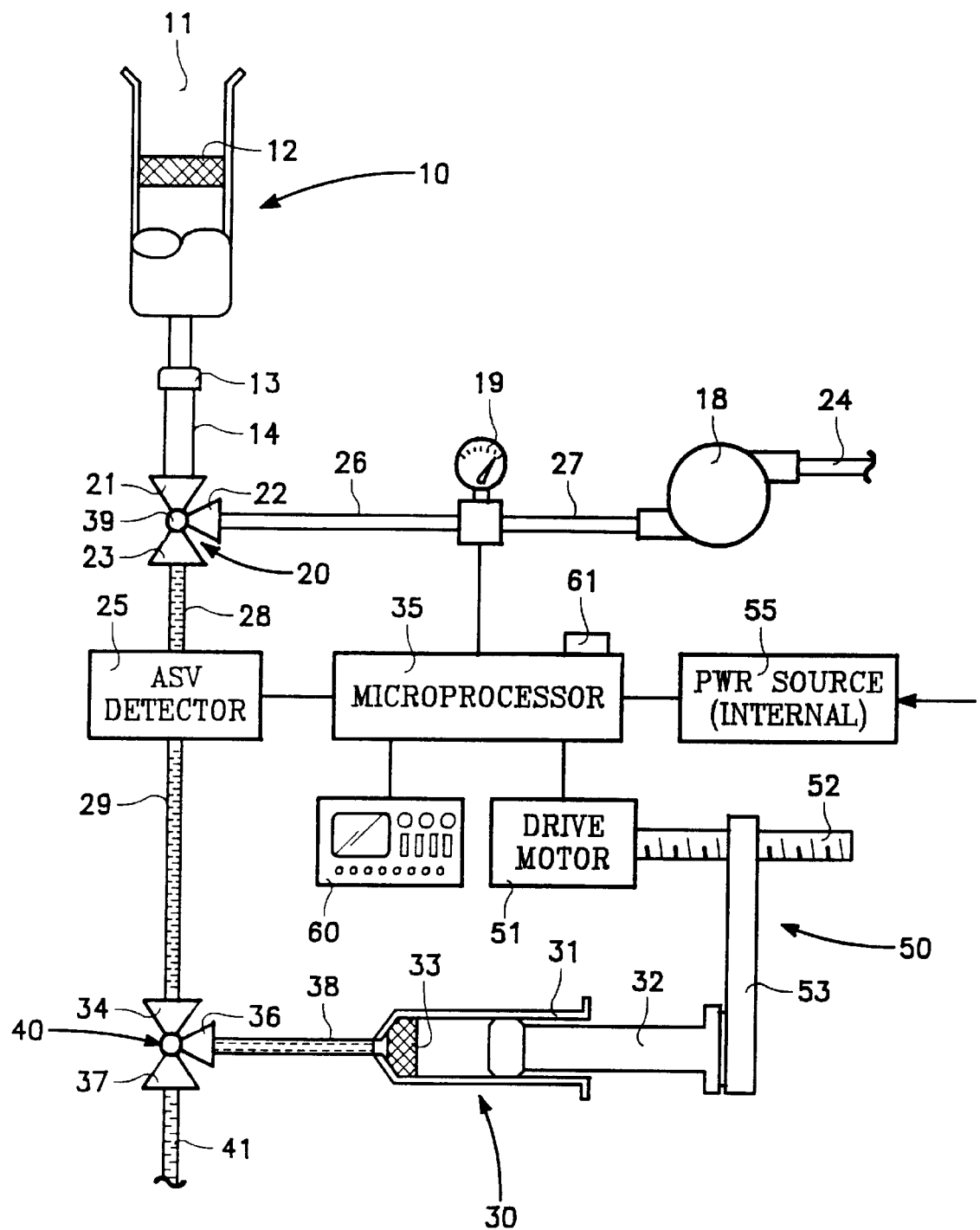

AUTOMATED AIRBORNE METAL ANALYZER

FIELD OF THE INVENTION

The present invention relates generally to a convenient, simplified, portable, and self-contained instrument for rapid collection, analysis, and measurement of low levels of airborne contaminants found in various environments. More specifically, the present invention is an improvement in field collection and measurement of airborne lead, cadmium, copper and mercury contamination. A field deployable instrument is described which is capable of automated airborne contaminant collection as well as precise, accurate, and automatic measurement of various contaminants in a wide range of in situ sampling environments.

DESCRIPTION OF THE RELATED ART

In the field of airborne contamination sampling, heavy metals and undesirable environmental toxins such as lead and mercury tend to be preferentially absorbed onto solid surfaces or absorbed into liquids, notably airborne solid particulates and suspended water droplets. Accurate airborne contaminant concentration levels are monitored through collection and analysis of these particulates and droplets absorbing contaminants and the free suspended contaminants.

Because contaminant samples are typically found in low concentrations within relatively large air volumes, preconcentration of these collected samples is a necessary practice among sampling and analysis methods. Typically used in air and liquid sampling applications, preconcentration increases the ability of detection instruments to identify very low contamination levels. Direct liquid absorption is commonly used to concentrate airborne contaminants by dissolving them into a liquid solvent. Subsequent analysis of this contaminant-rich solvent yields the detection or measurement of contaminants extracted from the air.

Handheld electro-monitor devices are known in the art of environmental monitoring and they currently enable their users to field analyze various liquid environmental and biological samples, commonly measuring contaminants in water and blood. These instruments provide portable analysis of fluid samples containing trace contaminants of undesirable toxins such as lead and mercury using electrochemical analysis methods, such as anodic stripping voltammetry. Portability and simplicity are key advantages of such apparatuses for field and lab analysis of liquid samples. These improvements are discussed in detail in U.S. Pat. No. 5,873,990, the entire disclosure of which is herein incorporated by reference.

A portable high-throughput liquid-absorption air sampler (PHTLAAS) capable of collection and direct liquid absorption of airborne contaminants is disclosed in U.S. Pat. No. 6,087,183. The PHTLAAS uses direct liquid absorption to collect and concentrate airborne contaminants into a liquid solvent and then subsequently analyze them to detect and measure dissolved airborne contaminant concentrations. The apparatus uses a fan to blow contaminant rich air through a small diameter tube and into its interior walls, which are wetted with a film of solvent. The fan directs the sample airflow into the liquid film, thereby impinging the airborne contaminants and contacting them with solvent. The contaminants are then dissolved by the solvent, which is preferentially selected for its ability to dissolve the airborne contaminants. The solvent is then collected and analyzed using an instrument to measure contaminant concentration.

While OSHA does not specify a particular method for monitoring respirable lead, it does set a performance standard for any method chosen. These codified standards, the OSHA General Industry Standard for Lead and the Construction Industry Standard for Lead, 29 CFR 1910.1025(d)(9) and 29 CFR 1962.62(d)(9), respectively, provide requirements for the airborne lead analyzer. Compliance with the OSHA General Industry Standard for Lead requires the method for determining airborne lead concentration to have a +/−20% accuracy within 95% confidence limits and result in greater than 80% recovery of the airborne lead for analysis. The standard is a major driving force behind innovation in the field because available technology struggles to meet this standard.

At present, airborne monitoring is a two step process often using two separate instruments to first collect and concentrate samples and then analyze them. The two instrument process creates unnecessary complications and hinders rapid return of test results. Additionally, the minimization of wastes generated from collection and subsequent analysis of potentially dangerous pollutants is not addressed by available technology.

SUMMARY OF THE INVENTION

The present invention is directed to both an apparatus and a method for accurate and reliable measurement of airborne contamination yielding a unit contaminant per unit volume sampled air measurement, while at the same time minimizing the generation of hazardous wastes as a by-product of the collection and analysis process.

One object of the present invention is to provide a singular, self-contained instrument for automatic airborne contaminant collection, concentration, measurement, and near real-time analysis within a self-contained instrument.

In the preferred embodiment, the collection system comprises an air pump for drawing sample air through an inlet tube, filter, and a flow meter. The air filter is a membrane filter with a 25 mm×0.8 micron pore size with a capture efficiency of 99.99%. In the preferred embodiment, the high efficiency filter satisfies OSHA requirements for capture efficiency and thereby improves accuracy shortcomings of alternative collection systems.

Additionally, the preferred embodiment permits calculation of contaminant concentration in units of parts per million (ppm) or parts per billion (ppb), which is another object of the invention. The preferred embodiment not only uses an air pump capable of moving high volumes of sample air through the collection system to offer high contaminant capture, but also uses a flow meter to simultaneously measure the airflow volume and returns faster results than available in alternative two step technologies. The preferred embodiment displays the resulting calculated values on an instrument mounted LCD on the face of the unit and also enables the data to be downloaded to a personal computer using an attached RS-232 interface data-port.

Another object of the present invention is to provide an instrument capable of performing analysis on both pre-collected test samples and near real-time samples. To achieve this object, the preferred embodiment features an inlet flange for detachably connecting an inlet tube module. This feature gives the present invention the flexibility to collect contaminant samples for immediate analysis or to analyze previously collected contaminant samples, which were collected by the present invention or by other collection devices. In the preferred embodiment, the apparatus may readily accept personal breathing zone monitors for analysis and measurement of contamination acquired by personnel using the monitors.

In the preferred embodiment, the concentration system is comprised of a user selected analysis media and a system of tubing connecting the inlet air filter, a syringe pump, the scrubbing media, and the measurement and analysis system. Chief among selection criteria for the analysis media is its ability to solubilize proscribed contaminants, but also include among other concerns, cost, disposal concerns, and availability.

To satisfy another objective of the invention, the preferred embodiment uses a metal removal media or device to minimize hazardous waste byproducts and accumulated collected lead particles. To achieve this objective, the preferred embodiment uses a pump, which, may be, for example, syringe pump, to pull contaminant-rich analysis media through an ion-exchange media after analysis of a contaminant sample is complete. The ion-exchange media cartridge binds contaminants dissolved within the analysis media within the cartridge and prevents contaminants from remaining soluble in the analysis media. As a result, waste is minimized and the analysis media can be reused.

In the preferred embodiment, the syringe pump acts as a reservoir for the analysis media, both prior to concentrating contaminants trapped in the air filter and also after scrubbing the contaminant from the analysis media.

In the preferred embodiment, the apparatus uses annodic stripping voltammetry (ASV) to measure solubilized contaminants in the analysis media. However, other methods for measurement of contaminant are contemplated, such as chemilunescence, colorimetrics, as well as other electrochemical detection devices and not solely ASV devices.

In the preferred embodiment, the apparatus may operate using a source of external alternating current. Additionally, the preferred embodiment has a rechargeable internal battery within the apparatus, giving the apparatus portability for field use.

Additional objects, advantages and novel features of the invention will be set forth in part in the description which follows, and will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention the attached diagram shows the preferred embodiment thereof, and from an inspection of which, when considered in connection with the following description, the invention, its construction and operation, and many of its advantages should be readily understood and appreciated.

DETAILED DESCRIPTION OF THE DRAWINGS

Referring to the schematic diagram of the preferred embodiment of the present invention, it will be readily apparent to one skilled in the art of the features, aspects and advantages supplied by the improvements offered.

In operation of the preferred embodiment, the air to be sampled, which contains trace amounts of airborne contamination, is drawn through an inlet module 10, which is a hollow tube having an inlet orifice 11, an internal filter 12, and an outlet orifice flange 13. The outlet orifice flange 13 is removably attached to a gas/liquid connector tube 14 leading to a three-way valve inlet 21 of a first three-way valve 20.

The first three-way valve 20 has a first outlet 22, which is ducted to a flow meter 19 via tube 26. The flow meter 19 is then ducted to an air pump 18 via tube 27. The first three-way valve 20 has a flow selector 39, which selectively opens the first outlet 22 while closing a first inlet/outlet 23. During air sampling, the air pump 18 pulls the sample air through the inlet module 10, the dual phase connector 14, the first outlet 22 of the first three-way valve 20, the flow meter 19, and the air pump 18 itself The air sample is then exhausted at an air pump exit tube 24.

It should be understood that three way valve 20 is not a necessary component of the present invention. The user may replace valve 20 with a tee and a two way valve on the airline.

During sample collection, the first three-way valve 20 permits air to travel through the inlet module 10, the flow meter 19, and the air pump 18, while the flow meter 19 generates a data signal representative of the volume of air sampled. The flow meter 19 sends this data signal to a microprocessor 35, which is connected to flow meter 19.

The first three-way valve 20 has a first inlet/outlet 23 ducted to an annodic stripping voltammetry (ASV) detector 25 via tube 28. The ASV detector is ducted to the inlet 34 of a second three-way valve via tube 29. This ASV detector 25 is also connected to the microprocessor 35. The second three-way valve 40 has a first inlet/outlet 36 connected to a syringe pump module 30 via tube 38, and a second inlet/outlet 37 that acts as an analysis media inlet/outlet 41 for charging and draining the system of analysis media. The second inlet/outlet 37 of the second three-way valve 40 leading to the analysis media charge inlet/outlet 41 is normally closed except for charging or draining the system.

It should be understood that valve 40 is not a necessary component of the present invention.

The syringe pump module 30 is comprised of a piston 32, a syringe housing 31, and a scrubber ion-exchange resin cartridge 33. A syringe drive module 50 operates the syringe pump module 30 and consists of a drive motor 51 having a drive shaft 52, and a drive block 53 which engages the drive shaft 52 of motor 51 such that rotation of shaft 52 moves drive block 53.

Once a contaminant rich air sample has been drawn through the inlet module 10, leaving a collected contaminant sample in the inlet filter 12, the microprocessor 35 activates the flow selector 39 of the first three-way valve 20, which closes the first outlet 22, opens first inlet/outlet 23, and leaves the three way inlet 21 open. Analysis medium stored in the syringe pump module 30 is injected into the inlet module 10 using the syringe drive module 50. Microprocessor 35 sends an electrical signal to activate drive motor 51. Once activated, the drive motor 51 rotates shaft 52 moving block 53 and pushing piston 52 inward within housing 31, which applies pressure to the analysis medium. Analysis medium is forced through second three-way valve 40, tube 29, ASV detector 25, tube 28, first three-way valve 20, and into inlet module 10 where the analysis media saturates the inlet filter 12 thereby solubilizing any contaminant trapped therein. After a timed period allowing complete solubilization, the microprocessor activates 35 the ASV detector 25 to begin analysis by activating a series of electrodes which electro-chemically draws the solubilized contaminant through the gas/liquid connector tube 14, the first three way valve, and tube 28. The ASV detector 25 measures contaminants present in the analysis medium and generates a data signal representative of the quantity of contaminants present. The ASV detector 25 then sends this data signal to the microprocessor 35, to which the ASV detector 25 is connected.

Once the air sample volume data signal and the contaminant concentration data signal are received, the microprocessor 35 calculates the unit contaminant per unit volume air sample and sends this information to a display and control unit 60 and alternatively sends the information to a data exchange port 61.

Upon completion of the process, the microprocessor 35 directs the syringe drive module 50 to withdraw the syringe pump piston 32 thereby drawing all contaminant-rich analysis medium into the syringe housing 31 through the scrubber medium cartridge 33 to remove solubilized contaminants from the analysis medium. Subsequently, the process may be repeated.

The metal removal cartridge 33 may be a separate device or may be located within the pump.

The second three-way valve 40 and the charge inlet/outlet 41 are used to drain the system of analysis medium and for charging a system with liquid analysis medium on startup.

The microprocessor 35, the ASV detector 25, the display and control unit 41, the syringe drive motor 51, the air pump 18, and the flow meter 19 are powered by a power source 55.

Although the present invention has been described in considerable detail with reference to certain preferred versions thereof, other versions are possible. Therefore the spirit and scope of the appended claims should not be limited to the description of the preferred versions contained therein.

It is claimed:

1. A portable apparatus for automatic collection, sampling, and analysis of airborne contamination comprising:
   (a) an inlet tube module comprising an inlet orifice, an inlet air filter within said inlet orifice, and an outlet orifice flange, said inlet air filter being adapted for capturing said airborne contaminants contained within gases collected by said portable apparatus;
   (b) a first three way valve comprising an inlet detachably connected to the outlet orifice flange of said inlet tube, a first outlet, a first inlet/outlet, and a flow selector, wherein the flow selector of said first three way valve closes the first outlet of said first three way valve which opens the first inlet/outlet of said first three way valve;
   (c) a flow meter comprising an inlet and an outlet, the inlet of said flow meter being connected to the first outlet of said first three way valve, said flow meter being adapted for volumetric measurement of said gases flowing from said inlet tube module through said flow meter, said flow meter generating signal data representative of said volumetric measurement by said flow meter of said gases flowing therethrough;
   (d) an air pump comprising an inlet and an outlet, the inlet of said air pump being connected to the outlet of said flow meter, wherein said air pump draws contaminant rich air samples through said inlet tube module, said flow meter, and the inlet of said air pump;
   (e) a chemical analysis device having an inlet and an outlet, said inlet connected to the first inlet/outlet of said first three way valve, said outlet connected to a bi-directional pump;
   (f) said bi-directional liquid pump connected to said analysis device, said bi-directional pump adapted for storing liquid;
   (g) a liquid analysis media stored within said bi-directional pump, said bi-directional pump supplying said liquid analysis media to said inlet filter, said liquid analysis media dissolving said airborne contaminants trapped in said inlet filter, said liquid analysis media forming a contaminant rich analysis media upon dissolution of said airborne contaminants trapped in said inlet filter;
   (h) said bi-directional pump drawing said contaminant rich analysis media from said inlet tube module to said chemical analysis device;
   (i) said chemical analysis device performing an analysis of said airborne contaminants dissolved in said contaminant rich analysis media and providing analysis data representative of the analysis performed by said chemical analysis device on said airborne contaminants dissolved in said contaminant rich analysis media;
   (j) a scrubber media positioned within said bi-directional pump, said bi-directional pump drawing said contaminant rich analysis media to said scrubber media, said scrubber media removing said dissolved contaminant from said contaminant rich analysis media;
   (k) a microprocessor connected to said flow meter to receive signal data and said chemical analysis device to receive said analysis data, said microprocessor using said signal data and said analysis data to calculate airborne contamination per unit of sampled air volume;
   (l) said microprocessor having a display and a control panel, the control panel of said microprocessor displaying values for the airborne contamination per unit of sampled air volume calculated by said microprocessor, said control panel allowing an operator to control operation of the collection, sampling, and analysis of said airborne contamination by said portable apparatus.

2. The portable apparatus as recited in claim 1, wherein the apparatus has a power source comprising a source of alternating current and a transformer, said transformer being connected to said source of alternating current, said transformer adapted for conversion of said source of alternating current to a source of direct current, said source of direct current being connected to said microprocessor.

3. The apparatus as recited in claim 2, wherein the power source of said apparatus further comprises an integrated rechargeable battery for providing direct current and adapted for recharge using said source of alternating current.

4. The apparatus as recited in claim 1, wherein the microprocessor has a data-port adapted for data exchange with an external computer.

5. A method for automatically collecting, sampling, and analyzing airborne contaminants, said method comprising the steps of:
   a) initiating a sampling process by setting controls on a control and display panel which corresponds to a sampling program within a microprocessor of a collection and analysis apparatus, said controls when set generating input selection signals;
   b) providing said input selection signals to said microprocessor, wherein said microprocessor, responsive to said input selection signals, generates function commands and then provides said function commands to a first three-way valve, bi-directional pump, and an air pump to control operation of said first three-way valve, said bi-directional pump, and said air pump during said sampling process;
   c) drawing an sample from a selected air mass containing airborne contaminants through a filter using said air pump to draw said air sample through said filter, said filter being located within an inlet tube module;

d) arresting and collecting said airborne contaminants within said filter;

e) recording the volume of air sample having passed through said filter using a flow meter;

f) sending a first set of electronic signals to said microprocessor representative of the volume of said air sample recorded by said flow meter;

g) injecting a solvent analysis media into said inlet tube module using a bi-directional pump to supply said inlet tube module with said solvent analysis media;

h) saturating said filter with said solvent analysis media;

i) dissolving said airborne contaminants collected in said filter into said solvent analysis media creating a contaminant rich solvent analysis media;

j) analyzing and measuring the content of said airborne contaminants within said contaminant rich solvent analysis media using a chemical analysis device;

k) sending a second set of electronic signals to said microprocessor representative of an analysis and measurement of said airborne contaminants within said contaminant rich analysis media;

l) calculating airborne contaminant per unit volume using said microprocessor which processes said first set of electronic signals and said second set of electronic signals to calculate said airborne contaminants per unit volume; and m) displaying said measurement and calculations on a liquid crystal display.

6. The method of claim 5 further including the step of regenerating and reusing said analysis medium, said method comprising the steps of:

a) drawing a contaminant rich analysis medium through an ion exchange scrubber medium using said bi-directional liquid pump;

b) removing dissolved airborne contaminants from said contaminant rich analysis medium using said scrubber medium; and c) reusing analysis medium for subsequent sampling operations within the apparatus by repeating the method of claim 5.

7. The method of claim 5 further including the step of analyzing alternate samples by disconnecting the inlet module unit sample in place of said inlet tube and replacing the inlet module with an alternate inlet module, said inlet module containing contaminants sampled previously extracted.

8. The method of claim 5 further including the step of transferring data collected in a microprocessor to an external computer using an integrated data transfer port where data is transferred electronically.

* * * * *